United States Patent [19]

Bundle et al.

[11] Patent Number: 4,831,126

[45] Date of Patent: May 16, 1989

[54] **ANTIGENIC POLYSACCHARIDE SPECIFIC TO *BRUCELLA ABORTUS* AND *YERSINIA ENTEROCOLITICA* SEROTYPE 0:9**

[75] Inventors: David R. Bundle; Malcolm B. Perry; John W. Cherwonogrodzky, all of Ottawa; J. Robert Duncan, Nepean, all of Canada; Martine G. Caroff, Meudon de la Foret, France

[73] Assignee: Canadian Patents & Development Ltd., Ottawa, Canada

[21] Appl. No.: 705,914

[22] Filed: Feb. 26, 1985

[30] Foreign Application Priority Data

Mar. 2, 1984 [CA] Canada .................................. 448768

[51] Int. Cl.[4] ........................ C08B 37/00; C07H 5/04; C12P 19/04; A61K 39/02

[52] U.S. Cl. ....................................... 536/53; 536/1.1; 536/18.7; 536/55.1; 435/101; 435/822; 424/92

[58] Field of Search ................ 536/1.1, 18.7, 53, 55.1, 536/55.3, 127, 17.2; 435/38, 101, 822; 436/543; 424/92, 123, 118

[56] References Cited

U.S. PATENT DOCUMENTS

| | | | |
|---|---|---|---|
| 3,148,120 | 9/1964 | Westphal | 424/92 |
| 3,342,684 | 9/1967 | Lembke et al. | 424/92 |
| 4,029,762 | 6/1977 | Galanos | 424/92 |
| 4,264,766 | 4/1981 | Fischer | 536/1.1 |
| 4,356,170 | 9/1982 | Jennings et al. | 424/92 |
| 4,397,959 | 8/1983 | Hechemy | 435/38 |
| 4,402,939 | 9/1983 | Fournier | 424/92 |
| 4,603,197 | 7/1986 | Kadoya et al. | 536/1.1 |
| 4,652,518 | 3/1987 | Makeza et al. | 536/1.1 |

FOREIGN PATENT DOCUMENTS

| | | | |
|---|---|---|---|
| 51-12921 | 1/1976 | Japan | 436/543 |
| 0988865 | 1/1983 | U.S.S.R. | 435/38 |

OTHER PUBLICATIONS

Hurvell; Acta Path. Microbiol. Scand. Section B, 81:105-112 (1973).

Hurvell et al; Acta Path. Microbiol. Scand. Section B, 81:113-119 (1973).

Berman et al; J. Clin. Microbiol. 11(4):355-362 (Apr. 1980).

Moreno et al; Infect. Immun. 31(1):214-222 (Jan. 1981).

Caroff et al; Infect. Immun. 46(2):384-388 (Nov. 1984).

Bundle et al; Infect. Immun. 46(2):389-393 (Nov. 1984).

Perry et al; Biochem. Cell Biol. 64(1):21-28 (1986).

Marx et al; Journal of Hygiene, Epidemiology, Microbiology and Immunology 18(4):429-431 (1974).

Marx et al; Ann. Microbiol. (Inst. Pasteur) 126 B, 435-445 (1975).

Sandulache et al; Ann. Microbiol. (Inst. Pasteur) 129 B, 425-435 (1978).

*Primary Examiner*—Ronald W. Griffin
*Assistant Examiner*—Nancy S. Carson
*Attorney, Agent, or Firm*—Alan A. Thomson

[57] ABSTRACT

The antigenic O-chain polysaccharides from *Brucella abortus* and *Yersinia enterocolitica* serotype 0:9 have similar structure, i.e. 1-2 linked 4,6-dideoxy-4-formamido-α-D-mannopyranosyl units. The antigen is more readily isolated from the Yersinia and may be chemically modified to have a hydrophobic moiety attached thereto. The antigen can be adsorbed or coupled to carriers suitable for immunoassay use such as ELISA and RIA. A monoclonal antibody capable of specifically binding to *B. abortus* and *Y. enterocolitica*, has been produced. Assay procedures and kits therefor, are described.

12 Claims, No Drawings

ANTIGENIC POLYSACCHARIDE SPECIFIC TO *BRUCELLA ABORTUS* AND *YERSINIA ENTEROCOLITICA* SEROTYPE 0:9

This invention relates to means for the identification of *Brucella abortus* and Brucellosis infection. The specification is divided into four parts: (1) The structure of the O-chain of the phenol-phase soluble cellular lipopolysaccharide (LPS) of *Yersinia enterocolitica* serotype 0:9, (2) Demonstration of the chemical identity of monosaccharide units of LPS from *B. abortus* 119-3 and *Y. enterocolitica* serotype 0:9, (3) The serological identity of *B. abortus* and *Y. enterocolitica* 0:9 O-antigens determined by monoclonal antibodies and the use of the above-determined facts in, (4) Preparation of materials for diagnostic testing. The background of each part of the invention is considered within each part of the invention.

SUMMARY OF THE INVENTION

This invention is concerned with an antigenic polysaccharide specific for *Brucella abortus* and *Yersinia enterocolitica* serotype 0:9 comprising 1–2 linked 4,6-dideoxy-4-formamido-α-D-mannopyranosyl units and having a molecular weight above about 15,000. Such an antigenic polysaccharide may comprise about 100 of said mannopyranosyl units and a molecular weight of about 18,000, and may also have a hydrophobic moiety attached thereto. Such a hydrophobic moiety often being a fatty acid ester linked to the polysaccharide via the aliphatic chain. The hydrophobic moiety, when a fatty acid ester, may have the general formula: $-NH-(CH_2)_nCOOR$, where R is a lower alkyl group and n=7–17. A particular embodiment of such a fatty acid ester hydrophobic moiety has the formula: $-NH-(CH_2)_{11}COOCH_2CH_3$.

An antigen of the type herein described may be adsorbed onto or coupled to a hydrophobic carrier and such a hydrophobic carrier may be selected from hydrophobic polymers. A particular embodiment comprises such an antigen-carrier combination wherein the carrier is an ELISA plate.

A monoclonal antibody produced by hybridoma cells, the spleenderived parent cell of which has been induced by the antigenic polysaccharide herein described, said antibody being capable of specifically binding to at least one antigenic determinant of *B. abortus* or *Y. enterocolitica* serotype 0:9 may be produced.

A method of detecting the presence of the bacteria *B. abortus* may comprise: (a) providing a sample suspected of containing said bacteria, from, for example, a domestic animal; (b) contacting said sample with the monoclonal antibody or with fluorescent- or enzyme-labelled derivatives thereof, and (c) observing whether agglutination or cell-labelling occurs, a positive agglutination or cell-labelling indicating the presence of said bacteria.

A method of detecting infections of *B. abortus* in animals may comprise: (a) providing a sample from the animal, for example, bovine milk or serum, (b) providing an antigen-coated carrier of the type herein described, (c) exposing the coated carrier to the sample to allow any antibodies in the sample to contact said antigen, and (d) detecting the presence of any specific antibodies attached to the antigen by an appropriate immunoassay, the presence of attached antibodies being a positive test for *B. abortus* infection.

In such a method, the immunoassay may take the form of an ELISA procedure.

A method of preparing antigen reagant suitable for detecting *B. abortus* or antibodies thereto, comprises, (a) growing *Y. enterocolitica* serotype 0:9 in a suitable growth medium, and recovering cells thereof, (b) isolating phenol-soluble lipopolysaccharide (LPS) from the cells, (c) cleaving the O-antigenic polysaccharide from the LPS with mild acid hydrolysis and removing the lipid portion, and (d) recovering the antigenic polysaccharide.

A method of producing antigen reagent linked to a hydrophobic moiety suitable for detecting *B. abortus* or antibodies thereto, comprises the steps (a) to (c) outlined above followed by (d) modifying O-antigenic polysaccharide resulting from step (c) to yield a side group capable of covalent bonding with reactive groups of a hydrophobic moiety (periodate oxidation to yeild aldehyde groups capable of such covalent bonding to amino groups is preferred) and, (e) reacting the product of step (d) with a hydrophobic moiety to yield such an antigen reagent.

A kit suitable for an immunoassay test for *B. abortus* or *Y. enterocolitica* serotype 0:9 may comprise: (a) assay plates coated with the antigen herein described, and (b) labelled antibodies from a suitable animal species to the antibodies under test.

A kit for an ELISA-type immunoassay test for *B. abortus* may comprise:

(a) assay plates coated with the antigen herein described, (b) anti-bovine or anti-human antibody from a suitable animal species, said antibody being labelled with an emzyme, and (c) an enzyme substrate which produces a colour reaction on exposure to said enzyme.

Structure of the O-chain of the phenol-phase soluble cellular lipopolysaccharide of *Yersinia enterocolitica* serotype 0:9

Cross-serological reactions between *Yersinia enterocolitica* serotype 0:9 and *Brucella abortus* antigens have been demonstrated using human sera, and the reactions have been confirmed with other antisera, and have been shown to extend to other Brucella species and also to *Vibrio cholerae* antigens. Sandulache and Marx (Ann. Microbiol. Inst. Pasteur, 129B, 1978) showed that the hot phenol-water extraction of *Y. enterocolitica* serotype 0:9 cells afforded two distinct lipopolysaccharides (LPS); one being found in the aqueous phase and the other in the phenol phase. It was further demonstrated that the phenol-phase LPS was responsible for the serological cross reactivity with *B. abortus* and *V. cholerae* antigens.

Because of the importance of Brucella, *V. cholerae* and *Y. enterocolitica* species in human and animal infections, it was considered that the determination of the structures of the cross reacting antigens would provide evidence for the molecular basis of the immunochemical reactivities and could assist in the possible development of protective vaccines and specific diagnostic reagents. Here we record the structural analysis of the O-antigenic chain of the serologically important LPS of *Y. enterocolitica* serotype 0:9 and the correlation of its cross-serological reactivities with Brucella species, with a common occurrence of 1–2 linked N-acylated 4-amino-4,6-dideoxy-α-D-mannopyranosyl units in the O-chains of their respective LPS.

Bacterial Culture

*Y. enterocolitica* serotype 0:9 (ADRI No. 21 from the collection of the Animal Diseases Research Institute, P.O. Box 11300, Station H, Nepean, Ontario, K2H 8P9) was grown in 4 L baffled conical flasks, each containing 2 L of 3.7% (w/v) brain heart infusion (Difco Laboratories), with rotary agitation (200 rpm) at 37° C. After 18 h growth, the contents of the flasks were adjusted to 0.2% (w/v) formaldehyde concentration and, after keeping overnight at 20° C., the cells collected (~ 4 g wet wt/L) by centrifugation, washed twice with 2.5% saline and finally collected by low speed centrifugation.

Lipopolysaccharide isolation and O-polysaccharide and core oligosaccharide preparation Washed cells of *Y. enterocolitica* serotype 0:9 were extracted by the lysozyme phenol-water method, and the well separated phenol and water layers in the cooled (4° C.) and centrifuged extracts were carefully collected, dialysed against running tap water until phenol free, and then lyophilized. The lyophilizates were taken up in 0.9% (w/v) saline and, following removal of insoluble material by low speed centrifugation, the clear solutions were subjected to ultracentrifugation (105,000 g) at 4° C. for 10 h. The collected clear deposited gels were subjected to repeated ultracentrifugation until they were judged pure by the carbocyanine dye assay. The lipopolysaccharide was found to be associated with the phenol layer.

To obtain O-polysaccharide and/or core oligosaccharide, 600 mg LPS, dissolved in 1.5% (w/v) acetic acid (400 mL), was heated in a boiling water bath for 2 h and the precipitated 'lipid A' was removed from the cooled solution by centrifugation. The lyophilized centrifugate was taken up in 0.05 M pyridinium acetate (pH 4.7, 5-6 mL) and following removal of more insoluble 'lipid A', the soluble products were fractionated by gel filtration on a column (2×40 cm) of Sephadex G-50 [trademark of Pharmacia Fine Chemicals] using the same buffer as the eluant. Fractions of the eluate (10 mL) were collected automatically and were analysed colorimetrically for neutral aldose, amino glycose, phosphate and 3-deoxyoctulosonate (KDO).

Periodate oxidation of polysaccharide

Polysaccharide (26 mg) in water (20 mL) was treated with sodium metaperiodate (80 mg) in water (5 mL) and after keeping at 4° C. for 48 h in the dark, ethylene glycol (150 μL) was added followed after 10 min by sodium borohydride (160 mg) and the mixture was left overnight at room temperature. The mixture was neutralized in the cold with acetic acid and following dialysis against tap water, the solution was passed through mixed Rexyn [trademark] 101 (H+) and Duolite [trademark] A4 (OH-) ionexchange resins (2 mL) and the eluates were lyophilized (~20 mg).

LPS and LPS fission products

Extraction of *Y. enterocolitica* serotype 0:9 cells (50 g dry weight) by a modified lysozyme phenol-water extraction procedure followed by purification of the LPS by repeated ultracentrifugations afforded an aqueous-phase LPS (1.48 g) and a phenol-phase soluble LPS (0.92 g). Both LPS were assessed to be pure from the fact that they gave a single peak at 460 nm in the carbocyanine dye assay, showed absence of absorption in the 210-300 nm region of the ultraviolet spectrum, and absence of ribose and amino acids in their hydrolysis products.

Polyacrylamide gel electrophoresis in buffered sodium dodecyl sulfate (SDS-PAGE) of the phenol-phase LPS showed a continuous band of silver nitrate staining product in the region of S-type LPS whereas, the water-phase LPS showed only a high mobility band typical of R-type LPS.

Partial fission of the phenol-phase LPS (600 mg) with hot dilute acetic acid afforded an insoluble 'lipid A' (180 mg) and gel-filtration of the water soluble products on Sephadex G-50 afforded an O-polysaccharide ($K_{av}$0.06, 214 mg), core oligosaccharide ($K_{av}$ 0.72, 34 mg), and a low molecular weight product ($K_{av}$ 1.0, 50 mg) identified by paper chromatography and GLC as essentially 3-deoxy-D-manno-octulosonic acid.

O-polysaccharide (phenol-phase LPS)

The phenol-phase O-polysaccharide was readily soluble in water having $[\alpha]_D+27.7°$ (c, 0.2 in water). Anal. found: C, 44.53; H, 6,58; N, 6.2%; Ash, nil. $^{13}$C-NMR data for the O-polysaccharide and its N-deacylated and N-acetylated derivatives are recorded in Table 1.

Partial C coupled $^{13}$C-NMR: 166.17 (d, 1C, $^1J_{C,H}$ 197.4 Hz, NHCHO), 101.75 (d, 1C, $^1J_{C,H}$ 173.4 Hz, C-1), 53.15 (d, 1C, $^1J_{C,H}$ 144.6 Hz, C-4), 18.07 (q, 1C, $^1J_{C,H}$ 127.4 Hz, C-6). Partial $^1$H-NMR ($D_2O$, 70° C.): 8.21 (s, 1H, NHCHO), 5.22 (bs, 1H, H-1), 1.27 (bd, 3H, H-6).

TABLE 1

C-NMR shifts (ppm) of the original and modified O—polysaccharide of *Y. enterocolitica* serotype 0:9

| Carbon Atom | O—poly-saccharide | N—deacylated O—poly-saccharide | N—acetylated O—polysaccharide |
|---|---|---|---|
| C-1 | 101.75 | 101.84 | 103.45 |
| C-2 | 78.25 | 77.79 | 79.91 |
| C-3 | 69.44 | 67.91 | 70.99 |
| C-4 | 53.15 | 55.18 | 55.93 |
| C-5 | 68.83 | 67.91 | 70.71 |
| C-6 | 18.07 | 17.97 | 19.64 |
| NHCHO | 166.17 | — | — |
| $NHCOCH_3$ | — | — | 177.67 |
| $NHCOCH_3$ | — | — | 25.03 |

Alkaline hydrolysis of the native O-chain (6 mg) followed by acidification (M $H_2SO_4$) and ether extraction gave formic acid as the only low molecular weight fatty acid detectable by GLC. The alkaline N-deformylated and N-acetylated O-chain (60 mg) on hydrolysis at 20° C. for 16 h with anhydrous hydrofluoric acid (1.5 mL) gave a single major product having $[\alpha]_D+15°$ (c, 0.22 in water) which gave a single spot on paper chromatography ($R_{Gal}$ 2.42) with the same mobility as 4-acetamido-4,6-dideoxy-D-mannose. The $^{13}$ *C-NMR* spectrum of the glycose was identical with that of authentic 4-acetamido-4,6-dideoxy-L-mannose and the reduced ($NaBD_4$) and acetylated glycose on GLC (program A) gave a single peak with $T_{GA}$ 1.31 whose mass spectrum and GLC retention time were identical with that of 1,2,3,5-tetra-O-acetyl-4-acetamido-4,6-dideoxy-L-mannitol-1-d.

Hydrolysis of the native O-chain with M $H_2SO_4$ or 2M HCl resulted in a black solution which on glycose analysis by the GLC alditol acetate method was found to contain: D-galactose, 0.49%; D-glucose, 1.5%; L-glycero-D-manno-heptose, 0.6%; D-glycero-D-manno-heptose, 1.7%; KDO, 0.4%; and 2-amino-2-deoxy-D-galactose, 0.7%.

The methylated and hydrolysed (HF) native O-chain afforded a product which after reduction ($NaBD_4$) and acetylation on GLC (program B) gave a single peak ($T_{GM}$ 8.20) which had the same retention time and gave the same mass spectrum as 1,2,5-tri-O-acetyl-4,6-dideoxy-3-O-methyl-4-(N-methylformamido)-D-mannitol-1-d.

The product obtained after treatment of the native O-chain with periodate followed by borohydride reduction and subsequent attempted hydrolysis with hot dilute acetic acid was found on Sephadex G-50 gel filtration to be eluted at the void volume of the column and the collected material was found to have $[\alpha]_D+26°$ (c, 0.1 in water) and to give a $^{13}$C-NMR spectrum identical with that of the original O-chain. The N-deformylated O-chain, oxidized by periodate, reduced and hydrolysed under the same conditions as those described above gave only products eluting in the low molecular weight elution region of the Sephadex G-50 gel filtration column.

In immunodiffusion, both the alkali treated Y. enterocolitica serotype 0:9 LPS and its O-chain gave strong precipitation lines against bovine antiserum to B. abortus cells and rabbit antiserum to Y. enterocolitica serotype 0:9 cells whereas the alkali treated water-phase LPS of Y. enterocolitica serotype 0:9, and the N-deformylated (NaOH) O-chain showed no precipitin reaction. The N-acetylated O-chain prepared by selective acetylation of the N-deformylated O-chain showed a strong precipitin line against the two antisera used.

Extraction of Y. enterocolitica serotype 0:9 cells by the lysozyme phenol-water method afforded two distinct LPS; one was found exclusively in the phenol layer and the other in the water layer. Our main attention was directed to the phenol-phase LPS because we found that it contained major antigenic determinants of the bacterium and it was responsible for serological cross reactions with B. abortus and V. cholerae specific antigens.

The phenol-phase LPS was obtained in 1.8% yield based on dry weight of cells and it was considered to be pure by physical and chemical criteria. On mild acid hydrolysis the LPS afforded a 'lipid A' (30%) and on gel filtration of the water soluble products an O-polysaccharide chain (35.6%), a core oligosaccharide (5.7%) and a low molecular weight fraction containing essentially 3-deoxy-D-manno-octulosonic acid (ca 6%) was obtained. The above hydrolysis data are typical of a S-type LPS and, furthermore, PAGE-SDS of the LPS showed it to give a slow mobility continuous silver staining band in the S-type LPS region, typical of a LPS having an O-chain composed of a uniform homopolymer composed of a single type glycosyl repeating unit.

Hydrolysis of the O-chain with dilute sulfuric or hydrochloric acid rapidly afforded a black solution indicating that extensive decomposition had taken place. Analysis of the glycoses liberated under these conditions showed the presence of D-galactose, D-glucose, L-glycero-D-manno-heptose, D-glycero-D-manno-heptose, KDO and 2-amino-2-deoxy-D-galactose (1:3:1:3:1:1) in a total yield of 5.2% and these glycoses probably represent the terminal core components of the O-chain. It was evident from the yields of hydrolytic products that the main components of the O-chain was being lost under the conditions used. Attempted methanolysis of the O-chain with 2.5% methanolic hydrogen chloride at 100° C. resulted in N-deacylation with the production of free amino groups but leaving the polymer in an essentially undegraded form as evidenced by its unchanged elution at the void volume of the Sephadex G-50 column.

Trial experiments revealed that the N-acetylated O-chain was completely hydrolysed on treatment at room temperature for 16 h with anhydrous hydrofluoric acid to yield a single paper chromatographically pure glycose which was identified as 4-acetamido-4,6-dideoxy-D-mannose from its specific optical rotation, paper chromatographic mobility and identity of its $^{13}$C-NMR spectrum with that of the authentic glycose and further, the identity of the GLC retention time and mass spectrum of the reduced (NaBD$_4$) and acetylated glycose with that of an authentic specimen of 1,2,3,5-tetra-O-acetyl-4-acetamido-4,6-dideoxy-L-mannitol-1-d made in this laboratory.

The $^{13}$C-NMR spectrum of the native O-polysaccharide showed seven strong signals and a number of very weak signals, as expected for an O-antigen having a single regular repeating monosaccharide unit linked to a core oligosaccharide. The observed low field signal (166.7 ppm) can be assigned to the carbonyl of the N-acylated group while the single signal at 101.75 ppm in the anomeric carbon region indicates that a single type of glycosyl linkage is present in the O-chain. The remaining assignment of signals (Table 2) is based on the identification of the repeating unit as the N-acylated derivative of 4-amino-4,6-dideoxy-D-mannopyranose and the subsequent identification of the linkage as being α1→2. The $^{13}$C-NMR spectrum of the derived N-acetylated O-chain appears to be identical with that reported by Redmond (Biochem. Biophys. Acta, 581, 1979) for the O-chain of the LPS of V. cholerae 569B (Inaba) while the spectra of the N-deacylated O-chain appears to be identical with the spectra of the N-deacylated O-chain of the LPS of V. cholerae serotypes Inaba and Ogawa, all of which have been determined to have O-chains of linear N-acylated 1→2 linked 4-amino-4,6-dideoxy-α-D-mannopyranosyl units.

The coupled $^{13}$C-NMR spectrum of the native O-chain showed a doublet in the carbonyl region (δ166.17, $^1J_{C,H}$ 197.4 Hz) which arises from a N-formyl substitution while the doublet (δ101.75, $^1J_{C,H}$ 173.4 Hz) found in the anomeric region possesses a $^1J_{C,H}$ coupling constant characteristic of the α-D-linked glycosyl residues. In support of the α-D- linkage assignment, the $^1$H-NMR spectrum showed a broad singlet at 5.22 ppm characteristic of the anomeric hydrogen of α-D-mannopyranosyl linkage and the observed specific optical rotation of the O-chain ($[\alpha]_D+27.7°$) is also consistent with the assigned configuration.

The inference that the amino group of the native O-chain has a formyl substituent from the observed splitting of the carbonyl signal in the coupled $^{13}$C-NMR spectrum was confirmed by the fact that formic acid was the only volatile acid detected by GLC after alkali treatment of the polysaccharide and by the fact that the low field singlet (δ8.21 ppm) seen in the $^1$H-NMR spectrum is very characteristic in its chemical shift for a N-formyl group.

While the above evidence leads to the conclusion that the O-chain is composed of 4,6-dideoxy-4-formamido-α-D-mannopyranosyl units, the position of the linkage remains to be chemically established. Methylated native O-chain could not be hydrolysed by the usual reagents without decomposition, however, it was readily hydrolysed by anhydrous hydrogen fluoride and the reduced (NaBD$_4$) and acetylated hydrolysis product on GLC-MS analysis gave a single major peak whose fragmentation pattern showed it to be a 1,2,5-tri-O-acetyl-4,6-dideoxy-3-O-methyl-4-(Nmethylformamido)-hexitol-1-d derivative indicating that the O-chain must be linked throughout by 1→2 linkages. In agreement with the 1→2 type linkage, the native O-chain was found to be resistant to oxidation by periodate whereas the N-deformylated O-chain was completely oxidized.

The combined chemical and physical evidence leads to the conclusion that the O-antigenic chain is a linear polymer of 1→2 linked 4,6-dideoxy-4-formamido-α-D-mannopyranosyl units terminated at the reducing end by core residues.

The phenol-phase LPS after mild alkali treatment to remove O-acyl fatty acids gave cross precipitin reaction in immunodiffusion against bovine antiserum prepared against killed B. abortus cells, against rabbit antiserum against killed Y. enterocolitica serotype 0:9 cells, and against mouse monoclonal antibody selected with phenol-phase LPS. That the antibody was directed against the O-chain of the LPS was shown by the fact that the O-chain itself gave a single strong precipitin line in immunodiffusion against the three antisera. The N-deformylated O-chain failed to give a precipitin line with the antisera, however, it was found that the N-acetylated O-chain prepared by selective acetylation of the N-deformylated O-chain appeared to have the same positive serological activity as the native O-chain.

In other studies made in this laboratory, we found that the phenol-phase LPS isolated from B. abortus 119-3 on mild acid hydrolysis afforded an O-chain which by all chemical and $^{13}$C and $^1$H-NMR spectral analyses was identical to the O-chain of the phenol-phase LPS of Y. enterocolitica serotype 0:9.

Demonstration of the chemical identity of monosaccharide units of LPS from *B. abortus*1119-3 and *Y. enterocolitica* serotype 0:9

The antigen phenol-phase LPS isolated from *B. abortus* 1119-3 by the hot phenol-water extraction procedure, was shown by electrophoresis, hydrolysis, periodate oxidation, methylation and $^{1}H$ and $^{13}C$ nuclear magnetic resonance studies to be a S-type LPS which on mild hydrolysis afforded a 'lipid A' and a polysaccharide O-chain identified as a linear homopolymer of 1,2 linked 4,6-dideoxy-4-formamido-α-D-mannopyranosyl residues. The cross-serological reactivity of bovine antiserum to *B. abortus* 110-3 with the LPS of *Y. enterocolitica* serogroup 0:9 has now been related to the occurrence of 1,2-linked N-acylated 4-amino-4,6-dideoxy-α-D mannopyranosyl units in their respective O-chains.

Cell production and LPS isolation

*B. abortus* strain 1119-3 (obtained as a lyophilized culture from Dr. R. D. Angus, Reagents Section, Scientific Services Laboratory, National Veterinary Services Laboratories, P.O. Box 844, Ames, Iowa 50010, U.S.A.) was grown on Potato Infusion Agar in Roux flasks for 48 h at 37° C. as described in the NADL Diagnostic Reagents Manual 65A (U.S. Department of Agriculture, Agricultural Research Service, Animal Health Division, National Animal Disease Center, Ames, Iowa 50010, U.S.A.). The growth from each flask (approx. 1.5 g wet weight/flask) was suspended in 40 mL of 0.85% sodium chloride solution containing 0.5% (w/v) phenol.

Wet cells of *B. abortus* (100 g) were suspended in water (400 mL) and at 70° C. and 95% aqueous phenol (400 mL) at 70° C. was added and the mixture was stirred vigorously at 68°-70° C. for 15 min. The cooled (4° C.) mixture was centrifuged (5000 x g) for 8 h at 4° C. and the clear aqueous and phenol phases were carefully separated from the interfacial debris located as a discrete band at the water-phenol interface. The aqueous and phenol phase extracts were dialysed against running tap water and when phenol free, were lyophilized. The aqueous and phenol phase extracts were taken up in 1% (w/v) sodium chloride solution (30 m) and were subjected to ultracentrifugation (105,000 x g) at 4° C. for 12 h and the precipitated gels were taken up in distilled water and were lyophilized to yield the crude LPS.

Partial hydrolytic fission of LPS 0.5% solution of LPS in 2% (v/v) acetic acid were heated on a boiling water bath for 2 h and the precipitated 'lipid A' material was removed from the cooled solutions by low speed centrifugation and the aqueous solutions were lyophilized and the residues in 0.05 M pyridinum acetate buffer pH 4.7 (3 mL) were fractionated on Sephadex G-50 columns.

Nuclear magnetic resonance (NMR)

Carbon-13 NMR ($^{13}C$-NMR) spectra were recorded on samples in $D_2O$ contained in 10 mm diameter tubes at 30° C. with a Varian CFT-20 spectrometer operating at 20 MHz in the pulsed Fourier transform mode with and without proton decoupling. Chemical shifts are reported downfield from external tetramethylsilane. Proton magnetic resonance ($^{1}H$-NMR) spectra were recorded on a Varian CFT-20 spectrometer operating at 79.9 MHz in the pulsed Fourier transform mode with the HOD signal suppressed by selective saturation using an inversion recovery pulse sequence. Sample in $D_2O$ were examined at 75° C. and chemical shifts are quoted downfield from internal 4,4-dimethyl sila(2,2,3,3-$^{1}H_4$) pentanonate.

The O-chain was a readily soluble white powder which had $[\alpha]_D+37.7°$ (c, 1,2 in water). Anal. found: C, 44.50; H, 6.55; N, 6.2; ash, 0.04%. The polysaccharide gave a $^{13}C$-NMR spectrum (30° C., 20 MHz) showing signals: 166.16 ppm, 101.81 ppm, 78.26 ppm, 69.52 ppm, 68.84 ppm, 53.15 ppm, and 18.07 ppm, which were subsequently assigned to the C atoms of 1,2 linked 4,6-dideoxy-4-formamido-α-D mannopyranosyl units.

The proton coupled $^{13}C$-NMR spectrum (30° C., 20 MHz) showed signals at 166.16 ppm (d, 1C, $^{1}J_{C,H}$ 197.3 Hz,NHCHO), 101.73 ppm (d, 1C, $^{1}J_{C,H}$ 173.3 Hz, C-1), 53.15 ppm (d, 1C, $^{1}J_{C,H}$ 144.6 Hz, C-4), and 18.07 ppm (q, 1C, $1J_{C,H}$ 127.4 Hz, C-6) for which the latter indicated assignments were made. The partial H-NMR spectrum of the O-chain (78° C., 79.9 MHz) showed signals at 8.18 ppm (s, 1H, NHCHO), 5.13 ppm (bd, 1H, $J_{1,2}$ 3.8 Hz, H-C-1), and 1.19 ppm (bd, 3H, $J_{5,6}$ 8 Hz, H C-6) for which the indicated assignments were made. The combined NMR data strongly suggested that the O-chain was composed of a single aminohexose repeating unit, probably containing 6-deoxy group and formylated amino group. The latter conclusion was verified from the fact that alkaline hydrolysis of the O-chain afforded 1 mol of formic acid per hexose residue as determined by GLC (program D) analysis.

Both the native O-chain and its N-acetyl derivative, prepared by selective N-acetylation of the alkaline deformylated polysaccharide, showed almost complete degradation on attempted hydrolysis with M sulfuric acid or 2M hydrochloric acid. The N-acetylated O-chain had $[\alpha]_D +32.0°$ (c, 1.3 in water) and its $^{13}$C-NMR spectrum (30° C., 20 MHz) showed signals at 177.66 ppm (NHCOCH$_3$), 103.43 ppm (C-1), 79.91 ppm (C-2), 70.97 ppm (C-3), 70.70 ppm (C-5), 55.91 ppm (C-4), 25.03 ppm (NHCOCH$_3$) to which the indicated assignments were made subsequent to its structural chemical identification.

The N-acetylated O-chain (40 mg) on treatment with hydrogen fluoride at 20° C. for 12 h afforded a single chromatographically pure glycose (14 mg) which after collection by preparative paper chromatography was found to have $[\alpha]_D +13°$ (c, 2.0 in water), gave a single spot on paper chromatography having R$_{Gal}$ 2.40 (solvent A) with the same mobility as authentic 4-acetamido-4,6-dideoxy-D-mannose. The identity of the glycose with the authentic samples was further indicated by the fact that its $^{13}$C-NMR spectrum (30° C., 20 MHz) was identical with that given by the equilibrium mixture of the authentic standard and furthermore the reduced (NaBD$_4$) and acetylated glycose on GLC-MS (program A) gave a single peak with T$_{GA}$ 1.33 whose mass spectrum and GLC retention time were the same as those given by a reference sample of 1,2,3,5-tetra-O-acetyl-4-acetamido-4,6-dideoxy-D-[1-$^2$H]-mannitol.

With the identity of the glycose unit of the O-chain established as the N-acyl derivative of 4-amino-4,6-dideoxy-D-mannose, its mode of linkage was established by methylation analysis. The methylated native O-chain hydrolysed with anhydrous hydrofluoric acid afforded a glycose which after reduction (NaBD$_4$) and acetylation gave a glycitol derivative which on GLC-MS (program B) analysis gave a single peak which had the same retention time (T$_{GM}$ 8.22) and gave the same mass spectrum as 1,2,5-tri-0-acetyl-4,6-dideoxy-3-0-methyl-4-(N-methylformamido-D-[1-$^2$H]-mannitol leading to the conclusion that the units are 1,2 glycosidically linked.

The evidence accumulated to date indicates that the O-chain is composed of 1,2 linked 4,6-dideoxy-4-formamido-D-mannopyranosyl residues. It was found that the O-chain was not cleaved on attempted periodate oxidation, a result consistent with the proposed structure and the fact that all the potential amino groups are N-formylated. The presence of the N-formyl, indicated by the release of formic acid on alkaline hydrolysis of the native O-chain, is further confirmed from the observed doublet of the carbonyl carbon (166.16 ppm, $^1J_{C,H}$ 197.3 Hz) seen in the coupled $^{13}$C-NMR spectrum and the singlet low field signal seen at 8.18 ppm in the $^1$H-NMR spectrum.

The positive specific optical rotation of the O-chain considered in conjunction with the coupling constant of the anomeric carbon atom (101.73 ppm, 1C, $^1J_{C,H}$ 173.3 Hz, C-1) which is characteristic of $\alpha$-D-glycopyranosyl residues in proton coupled $^{13}$C-NMR spectra, and the observed low field anomeric proton signal (5.13 ppm), characteristic of $\alpha$-D-mannopyranosyl residues in the $^1$H-NMR spectrum, lead to the conclusion that the native O-chain is a linear polymer of 4,6-dideoxy-4-formamido-$\alpha$-D-mannopyranosyl units linked 1,2 throughout.

While hydrolysis of the O-chain with hot dilute mineral acids (2M HCl or H$_2$SO$_4$, 6 h, 100° C.) caused complete destruction of the 4-aminoglycose component, the hydrolytic procedure afforded D-mannose (1.51%), D-glucose (1.01%) and 2-amino-2,6-dideoxy-D-glucose (quinovosamine-1.01%) identified by GLC of their TMS (−)-2-butylglycoside derivatives and by quantitative GLC (program A) analysis of the derived mannitol (T$_{GA}$ 0.90) glucitol (T$_{GA}$ 1.00) and 2-amino-2,6-dideoxyglucitol (T$_{GA}$ 1.40) acetates. It is probable that the D-glucose, D-mannose and 2-amino-2,6 dideoxy-D-glucose residues arise from the terminal 'core' and their total (3.56%) is compatible with an average O-chain length of ~96 aminoglycose units. The $^{13}$C-NMR spectrum and the SDS-PAGE electrophoresis results are similarly consistent with the proposition that the O-chain is essentially homopolymer of average chain length of 96–100 residues and that the core region forms a minor component. 3-deoxy-2-octulosonate could not be detected by either GLC or paper chromatographic methods in the phosphate-rich fraction eluted in the monosaccharide region obtained on Sephadex G-50 gel filtration of the water soluble products remaining after treatment of the LPS with hot dilute acetic acid. The failure to detect liberated 3-deoxy-2-octulosonate suggests that the cleavage of the LPS to yield a 'lipid A' material and a polysaccharide probably involves the hydrolysis of an acid labile glycosidic linkage other than that usually associated with 3-deoxy-D-manno-octulosonic acid. A second unusual feature of the LPS was the failure to detect any component aldoheptose.

That the serological specificity of the antibody in bovine antiserum prepared against B. abortus cells was directed to the O-chain of the phenol phase LPS was shown by the fact that strong single precipitin lines were observed in immunodiffusion of the serum against LPS and against purified O-chain.

In conclusion, it can be stated that the O-chain of B. abortus LPS and Y. enterocolitica serotype 0:9 LPS are identical and an examination of the molecular model of the O-chain shows that the cross reaction of polyclonal antiserum to other N-acylated derivatives of the O-chain is possible from a structural point of view.

The Serological identity of B. abortus and Y. enterocolitica 0:9 O-antigens determined by monoclonal antibodies Murine monoclonal antibodies were generated that bind the O-antigens of Y. enterocolitica 0:9 and B. abortus 1119-3. BALB/c mice were immunized with killed, whole cell vaccines and highly purified LPS preparations from each organism were used to screen for antigen specific hybrids. The Brucella vaccine, induced 56 antigen specific hybrids and ten of the highest antibody producing clones were selected for further study. Seven of these clones secreted IgG and three secreted IgM. A similar experiment employing the Yersinia vaccine resulted in 76 antigen specific hybrids, from which seven IgG secreting clones were selected for study. On the basis of ELISA, immunoprecipitation and agglutination methods, the Brucella and Yersinia clones demonstrated the serological cross reactivity of the two O-antigens, which is consistent with the structural identity revealed by chemical analysis.

In the preceding work, the chemical similarity of the O-polysaccharide chains of *B. abortus* and *Y. enterocolitica* was established. Earlier serological studies, especially by Lindberg and his co-workers (i.e. Acta Path. Microbiol. Scand., 81B, 1973) had pointed to the possibility of shared determinants in the lipopolysaccharides (LPS) of these bacteria. Various less well established serological cross-reactions have also been reported. A common feature of these studies was the use of polyclonal, immune sera, mostly from rabbits, with the attendant problems of cross-absorption for various cross-reacting antigens. The monoclonal antibody technique conveniently circumvents such problems and furthermore, monoclonal antibodies are considered ideal probes for detecting specific cell surface molecules.

It was decided, therefore, that monoclonal antibodies produced to the LPS of both *Y. enterocolitica* 0:9 and *B. abortus* would be particularly well suited for studies of the reported serological cross-reactions involving these and other Gram-negative bacteria. Furthermore, it was anticipated that selected monoclonal antibodies with defined binding characteristics may serve as useful reagents for the routine serological identification of these organisms.

Antigens

The bacterial strains, *B. abortus* 1119-3 and *Y. enterocolitica* 0:9 were those described above.

Vaccines consisted of bacterial cells in late log phase, phenol-killed (1% w/v of phenol), washed with PBS and suspended in PBS at $2 \times 10^8$ cells/ml. Lipopolysaccharides were extracted from bacteria grown in batch culture by the phenol-water method, and the phenol phase soluble LPS were purified by repeated enzyme digests and ultracentrifugation.

O-polysaccharides ('lipid A' free) were prepared from the respective LPS by mild acetic acid hydrolysis and subsequently, gel-filtration chromatography of the water soluble products.

Immunization

Female BALB/c mice (Charles Rivers Canada Inc., St. Constant, Quebec) 6-8 weeks old, were given 2 intraperitoneal injections one week apart and, following a 3-week rest, the mice received a final intravenous injection. All three injections consisted of $10^8$ *Y. enterocolitica* 0:9 or *B. abortus* phenol-killed cells in 0.01M phosphate-buffered saline, pH 7.0 (PBS).

Fusion and cloning

The fusion protocol was the modified procedure described by Kennett et al, (Curr. Top. Microbiol. Immunol. 81, 77-91, 1978) which combines the essential elements of procedures developed by Gafle et al (Nature 266, 550-552, 1977) and Gefter et al (Somatic Cell Genet. 3, 231-236, 1977). Spleen cells from two immunized mice were fused with the non-Ig-producing Sp2/O plasmacytoma cell line (Institute for Medical Research, Camden, N.J.) as previously described by Bundle et al (J. Immunol. 129, 678-682, 1982). Putative hybrids were screened by an enzyme-linked immunosorbent assay (ELISA) on culture supernatants (100 μl) 10 to 14 days post fusion. Hybrids exhibiting an absorbance reading greater than 0.3 against negligible background were cloned in "semi-solid agar" using mouse spleen cells as feeders. All hybrids were cloned twice to ensure stability prior to freezing cell samples and raising ascitic fluid.

ELISA screening

LPS-coated Linbro [trademark] EIA microtitration plates (Flow Laboratories, Mississauga, Ontario) were prepared by incubating with 100 μl/well of the appropriate LPS solution (10 μg/ml) in 0.05M sodium carbonate buffer, pH 9.8 for 3 h at 37°. Plates were stored, sealed at 4° until needed. ELISA testing of cell supernatants and ascitic fluid was carried out as described by Bundle et al. This employed an alkaline phosphatase conjugated goat anti-mouse IgM and IgG antibody preparation in conjunction with p-nitro-phenolphosphate substrate (Sigma) (1 mg/ml p-nitro-phenolphosphate disodium salt in 0.05M carbonate buffer, pH 9.8 containing magnesium chloride, $10^{-3}$M). Absorbance at 405 nm was read after 60 min at room temperature using a Titertek Multiscan (Flow Laboratories). Monoclonal Ig class was determined using the Hybri-Clonal EIA Mouse Antibody Screening Kit (Kirkegaard and Perry Laboratories Inc., Gaithersburg, Md., U.S.A.).

Ascitic fluid

BALB/c mice were primed by intraperitoneal injection of 0.5 ml 2,6,10,14-tetramethylpentadecane (pristane) one to four weeks prior to injection with 10 hybridoma cells. Ascitic fluid was tapped 7-10 days later and stored at -70°.

Whole cell agglutination

Whole cell agglutination was performed in Linbro 96-flat well microtitration plates (Flow Laboratories). To each well was added 100 μl of ascitic fluid diluted 1:10, 1:100 and 1:1000 in PBS, followed by 10 μl of a suspension containing $10^{10}$ *Y. enterocolitica* 0:9 or *B. abortus* cells per ml PBS. The suspensions were mixed, allowed to settle for 2 h at room temperature and agglutination scored by microscopic examination.

Immunodiffusion

Immunodiffusion plates were set up using 1% agarose, Induboise A37 (Fisher) in PBS. Ascitic fluids were added to the wells undiluted; antigen solutions (bacterial PS and alkali-treated LPS) were used at 1 mg/ml and 0.5 mg/ml concentrations. Precipitin lines were recorded following 24–48 h incubation at room temperature.

SDS-PAGE and immunoblots

LPS samples were subjected to SDS-PAGE according to the published method of Tsai and Fraser (op.cit.) and subsequently the gel was transblotted onto nitrocellulose. Transblots were run for 3 h at 60 V and 250 mA in the buffer, 25 mM Tris, 192 mM glycine containing 20% (v/v) methanol at pH 8.3. The nitrocellulose sheet was blocked with 2% BSA in Tris-saline, pH 7.4, for 18 h at 4°, then washed twice in Tris-saline, cut into appropriate strips and incubated with monoclonal antibody for 3 h at 4°. The monoclonal antibodies Ys. T9-5 and Ys. T9-6 were diluted 1:500 in Tris-saline, pH 7.4, for incubation. Nitrocellulose strips were washed three x 30 min in Tris-saline prior to incubation with a commercial goat anti-mouse horseradish peroxidase second antibody (BIO-RAD, Mississauga, Ontario) for 1 h at room temperature. Following 3 twenty-minute washes in Tris-saline, the nitrocellulose strips were developed in HRP colour development reagent, a solution of 4-chloro-1-naphthol (BIO-RAD) and after 1 h, LPS, to which monoclonal antibodies had bound, were seen as purple bands on an off-white background.

Results

BALB/c mice were immunized with killed, whole cells of *Y. enterocolitica* and *B. abortus* according to a protocol designed to maximize the number of IgG producing hybrids. This was achieved via optimal spacing of three injections, the last of which was given intraveneously three days prior to fusion, in order to maximize the number of antigen specific hybrids. In each case, spleen cells from two immunized mice were fused with a clone of the Sp2/O cell line used in this laboratory. Culture supernatants were assayed for antibody by ELISA employing as antigen, homologous LPS coated microtitration plates.

Yersinia 0:9 LPS specific hybrids occurred in 16% of the 433 wells with putative hybrids. Selection of hybrids for further study was based upon two criteria. First, the quantitiy of LPS specific antibody present in the culture supernatant as judged by optical density in ELISA, and second, but not exclusively, a binding affinity for *B. abortus* LPS coated ELISA plates. Two clones with unique specificity for Yersinia were selected together with five clones which showed strong cross-reactivity for the *B. abortus* LPS. Approximately 60% of the initial 76 Yersinia LPS specific monoclonal antibodies exhibited significant *B. abortus* activity.

In the Brucella fusion experiment, antigen specific hybrids were produced in 14% of wells showing hybrid growth and all 56 of these clones cross-reacted with the heterologous Yersinia LPS. Ten of the clones were established as stable lines by recloning and ascitic fluid raised with each cell line. It was shown by ELISA-based class analysis employing antigen coated plates and a commercial class specific second antibody, that of those selected, all antibodies generated by the Yersinia fusion were of the IgG class, while those from the Brucella experiment were predominantly IgGs (see Table 2).

Evaluation of the binding characteristics of the monoclonal antibodies to the O-antigen were performed on ascitic fluids and these results are recorded in Tables 3 and 4. ELISA end-point titrations were conducted for each antibody employing both Yersinia and Brucella LPS antigens. All of the antibodies B.ab. 1–10 (Table 4) showed similar ELISA titres with both the homologous and heterologous LPS. A similar picture emerged for the Yersinia clones, although clones Ys.T9-5 and Ys.T9-6 failed to react with the heterologous Brucella LPS. The virtual identity of titration curves with both homologous and heterologous LPS is illustrated for two representative monoclonal antibodies Ys.T9-2 and B.ab.-8. With the exception of clones Ys.T9-5 and Ys.T9-6 this was a general observation.

TABLE 2

Specific and Putative Hybrids in Response to Bacterial Vaccines

| Bacterial Vaccine | Putative hybrids: Wells plated | LPS-specific hybrids[a] | Class of recloned LPS-specific hybrids[b] IgG | IgM |
|---|---|---|---|---|
| *Y. enterocolitica* 0:9 | 433:576 | 76 | 7 | 0 |
| *B. abortus* 1119-3 | 385:576 | 56 | 7 | 3 |

[a] Determined by ELISA with homologous LPS antigen-coated plates
[b] Ig class determined by class-specific ELISA reagents.

TABLE 3

Characteristics of monoclonal antibodies to *Yersinia enterocolitica* 0:9

| Yersinia enterocolitica LPS-specific hybrids | Ig Class[a] | Immunodiffusion Yersinia alkali treated LPS | Yersinia PS | Brucella PS | ELISA titers[b] Yersinia LPS | Brucella LPS | Whole cell agglutination Yersinia | Brucella |
|---|---|---|---|---|---|---|---|---|
| Ys.T9-1 | G | − | − | − | $10^5$ | $10^5$ | + | + |
| Ys.T9-2 | G | + | + | + | $5 \times 10^4$ | $10^5$ | + | + |
| Ys.T9-3 | G | + | − | − | $5 \times 10^4$ | $5 \times 10^5$ | + | + |
| Ys.T9-4 | G | + | − | + | $5 \times 10^4$ | $10^5$ | + | + |
| Ys.T9-5 | G | + | − | − | $5 \times 10^4$ | − | + | − |
| Ys.T9-6 | G | + | + | − | $5 \times 10^4$ | − | + | − |
| Ys.T9-7 | G | − | − | − | $10^5$ | $3.2 \times 10^3$ | − | + |

[a] Ig class determined by class-specific ELISA reagents
[b] End point taken as the reciprocal of ascitic fluid dilution which after 1 hr gave an absorbance 0.1
[c] Results of agglutination at 1:100 dilution of ascitic fluid

TABLE 4

Characteristics of monoclonal antibodies to *Yersina enterocolitcia* 0:9

| Yersinia enterocolitica LPS-specific hybrids | Ig Class[a] | Immunodiffusion Yersinia alkali treated LPS | Yersinia PS | Brucella PS | ELISA titers[b] Yersinia LPS | Brucella LPS | Whole cell agglutination Yersinia | Brucella |
|---|---|---|---|---|---|---|---|---|
| B.ab.-1 | M | − | − | − | $10^4$ | $10^4$ | + | + |
| B.ab.-2 | G | − | − | − | $10^4$ | $10^4$ | + | + |
| B.ab.-3 | G | + | − | − | $10^3$ | $10^3$ | + | + |
| B.ab.-4 | G | + | + | + | $10^5$ | $10^5$ | + | + |
| B.ab.-5 | G | − | − | − | $5 \times 10^4$ | $10^5$ | + | + |
| B.ab.-6 | M | + | + | + | $5 \times 10^4$ | $5 \times 10^4$ | + | + |
| B.ab.-7 | G | + | + | + | $5 \times 10^4$ | $10^4$ | + | + |
| B.ab.-8 | G | + | + | + | $5 \times 10^4$ | $5 \times 10^4$ | + | + |
| B.ab.-9 | M | + | − | − | $10^5$ | $10^5$ | ± | ± |
| B.ab.-10 | G | + | + | + | $5 \times 10^4$ | $5 \times 10^4$ | + | + |

[a] Ig class determined by class-specific ELISA reagents
[b] End point taken as the reciprocal of ascitic fluid dilution which after 1 hr gave an absorbance 0.1
[c] Results of agglutination at 1:100 dilution of ascitic fluid Agglatination patterns with phenol killed Yersinia and Brucella cells were consistent with the ELISA titrations except for the monoclonal antibody Ys.T9-7, which agglutinated Brucella cells but not the homologous Yersinia cells. Also surprising was the observation that antibody B.ab.-9, an IgM, was a weak to non-agglutinating antibody despite its class and high ELISA titer (Table 4).

Summarized immunodiffusion results are presented in Table 3 and 4. Two patterns were observed, antibodies that could precipitate only LPS (Ys.T9-3, -5; B.ab.-3, -9), and those that could precipitate both LPS and O-chain polysaccharide (Ys.T9-2, -4; B.ab.-4, -6, -7, -8 -10). Antibody Ys.T9-6 distinguished the Yersinia and Brucella O-chain (Table 3).

LPS from *Y. enterocolitica* and *B. abortus* were subjected to SDS-PAGE and, initially using the silver staining method, an unresolved, continuous streak was observed. This pattern is characteristic for O-chains with a monosaccharide repeating unit. However, by judicious loading of the gel, it was possible to observe finely resolved bands for both LPS using the silver stain and, most effectively, by immunoblotting. The SDS-gel was transblotted and a cocktail of all Yersinia monoclonal antibodies Ys.T-1 to -7 was used, in conjunction with a goat-antimouse HRP conjugated antibody to visualize the LPS banding. Immunoblots performed in similar fashion with individual monoclonal antibodies Ys.T9-5 and -6 showed that these antibodies bound only to the S-type LPS molecules and not the core LPS devoid of O-chain.

Following cloning and production of ascitic fluid, more elaborate assays were conducted to establish the binding profile of each antibody. Thus, all of the monoclonal antibodies could be assigned to one of four specificity patterns.

Type 1—The antibodies which precipitated LPS, and O-chains of Yersinia and Brucella and exhibited high ELISA titres with homologous and heterologous antigens, in addition to agglutinating activity for both bacteria, Ys.T9-2, -4; B.ab.-4, -6, -7, -8 and -10, were clearly directed to antigenic determinants present along the length of the polymeric O-chain. The coincidence of the ELISA titration curves for two of these antibodies, Ys.T9-2 and B.ab.-8, are typical of this type of antibody and illustrate the fact that in serological terms, the O-chains of Brucella and Yersinia are identical.

Type 2—Ys.T9-1, Ys.T9-7, B.ab-1, -2 and -5, were agglutinating for both bacteria and exhibited good heterologous and homologous ELISA titres but did not precipitate the LPS nor the polysaccharides. Since they are cross-reactive in the Yersinia/Brucella system the specificity is to a common element, the O-chains, but because they are not precipitating, it is inferred that the determinant is univalent. In the streptococcus, Schalch et al (J. Exp. Med. 149, 923–937, 1979) have assigned such characteristics to chain end binding specificity and our antibodies of type 2 are similarly assigned.

Type 3—Two antibodies, Ys.T-5 and -6 (type 3), deliberately selected from the Yersinia fusion experiments because they failed to show ELISA titres with the heterologous, Brucella LPS were believed to be core specific antibodies. No such antibodies with unique Brucella activity were isolated from the fusion experiment with *B. abortus* as antigen. Despite the fact that core oligosaccharides are essentially univalent antigens, both Ys.T9-5 and -6 precipitated the core-containing Yersinia LPS. In order to clarify the specificity of these antibodies, Yersinia LPS was subjected to SDS-PAGE electrophoresis and the gel was transblotted onto nitrocellulose. Treatment of the nitrocellulose with either of the two monoclonal antibodies, Ys.T9-5 and -6, followed by a second antibody conjugated to HRP showed that LPS bearing O-chains and not core LPS (R-type LPS) was bound by the two antigens. This indicates that the portion of the O-antigen recognized is most probably an oligosaccharide portion which encompasses elements of both the O-chain and core. This would correspond to the semi-rough portion of LPS at the point where O-chain is linked to core. The ability to precipitate LPS derives from the multivalence generated by aggregation or micelle formation due to attached lipid. Thus, precipitation does not occur with the polysaccharide or either organism for Ys.T9-5 as expected, although antibody Ys.T9-6 does show a very faint precipitin line with the Yersinia LPS. Both antibodies do, however, consistently distinguish Brucella from Yersinia LPS in precipitation, agglutination and ELISA.

Type 4—The final class of antibodies, Ys.T9-3, B.ab.-3 and -9, which precipitate the LPS but not the polysaccharide antigens show similar ELISA and agglutination profiles. All demonstrate agglutination of *B. abortus* and *Y. enterocolitica* 0:9, although B.ab.-9 is only weakly positive at a dilution of 1:100, despite its IgM class. Since these antibodies are equally reactive with both heterologous and homologous LPS, the antigenic determinant recognized should reside in the O-chain. In fact, these antibodies may be similar to those of type 2 in recognizing chain end determinants. Precipitation of LPS by type 4 antibodies but not type 2 antibodies cannot be explained by the state of aggregation of the antigen but may be an intrinsic property of the antibodies.

Seventeen LPS specific monoclonal antibodies were generated from two fusion experiments which used either *B. abortus* or *Y. enterocolitica* 0:9 vaccines. Fifteen of these antibodies showed activity for the O-antigen of both organisms on the basis of ELISA and agglutination tests. Two antibodies with at least partial core specificity may be used to distinguish the Yersinia 0:9 LPS from the Brucella antigen. Thus, it is possible to serologically distinguish these two bacteria, which have a known serological cross-reactivity, by choosing the appropriate pair of monoclonal antibodies. Such tests could be based on either precipitation, agglutination or ELISA. These antibodies are being used to study the cell wall polysaccharide antigens of other Brucella strains. Type 1 antibodies were found to agglutinate smooth strains of *B. abortus, B. melitensis, B. neotomae, B. suis*, but not rough strains or *B. ovis* and *B. canis*. Type 4 antibodies have been used to differentiate biotypes of the same species (e.g. *B. abortus*) and can be used interchangeably with "anti-A anti-Brucella" rabbit serum (from Ames).

Preparation of materials for diagnostic testing

Diagnostic tests such as ELISA, RIA and fluorescent labelled antibody tests may be performed upon materials extracted from animals and humans suspected of carrying *B. abortus* and *Y. enterocolitica*. Such tests may comprise the following steps: (1) These antigenic polysaccharides specific for *B. abortus* and *Y. enterocolitica* serotype 0:9 comprise 1–2 linked 4,6-dideoxy-4-formamido α-D-mannopyranosyl units having a M.W. of above about 15,000. They usually comprise around 100 mannopyranosyl units and have a M.W. of about 18,000 and are isolated as herein described. (2) The antigenic polysaccharide is treated with periodate as herein described to yield aldehyde side groups as a result of periodateoxidation. (3) The product of step (2) is treated with a hydrophobic moiety such as a fatty acid ester of the type: $H_2N-(CH_2)_nCOOR$, where R is a lower alkyl group and n=7-17. We used $H_2N-(CH_2)_{11}-COOEt$. This yields a Schiff base.

(4) The product of step (3) is treated with a reducing agent, such as lithium cyanoborohydride, to yield the polysaccharide attached to a hydrophobic moiety with a chemically reduced link.

(5) The product of step (4) is adsorbed or coupled onto a hydrophobic carrier, usually a hydrophobic polymeric material which may be of the type used as ELISA plates. These treated carriers or plates may be stored and incorporated into a kit such as those used in ELISA, RIA and fluorescent labelled antibody tests.

(6) Testing involved (a) exposing the treated carrier or plate to material from the animal or human suspected to carry *B. abortus* or *Y. enterocolitica*, (b) removing unattached material by mild washing or rinsing, (c) (i) in the case of ELISA subjecting the test material resulting from (6) (b) to antibody (to the antibody under test) to which is attached a suitable enzyme. We tested bovine samples and employed goat antibody to bovine antibody, the goat antibody being linked to a suitable enzyme, in our case phosphatase. We subsequently added a suitable substrate for the enzyme to yield an easily measured change. Colourless paranitrophenolphosphate was employed and was hydrolyzed by the phosphatase bound successively through the goat antibovine antibody to the bovine antibody to the antigenic polysaccharide to the fatty acid ester to the hydrophobic ELISA plate. Hydrolysis yielded yellow paranitrophenol; (ii) in the cases of RIA and fluorescent labelled antibody tests, the antibody to the antibodies under test in respectively linked to a radiolabel or a material with fluorescent properties and these are employed as detection means.

A kit for an immunoassay test for *B. abortus* or *Y. enterocolitica* serotype 0:9 may comprise (a) assay plates coated with the antigenic polysaccharide herein described, usually of M.W. greater than about 15,000, preferably about 18,000, and modified with an attached hydrophobic moiety to facilitate attachment to the assay plate, and (b) labelled antibodies to the antibodies under test. In the case of an ELISA kit (b) is made up of anti-bovine or anti-human antibody from a suitable animal species, the antibody being labelled with an enzyme. In an ELISA kit, it is also useful to provide (c) an enzyme substrate that produces a detectable change, usually a colour change, an exposure to said enzyme.

Antibodies that distinguish *B. abortus* from *Y. enterocolitica* serotype 0:9 may be used in cases where doubt exists as to the infecting species.

The antigenic polysaccharide has been found to be similarly effective in detective and identifying *Brucella melitensis* and antibodies thereto. *B. melitansis* is a problem in some countries such as Spain.

We claim:

1. Antigenic polysaccharide specific to *Brucella abortus* and *Yersinia enterocolitica* serotype 0:9 comprising about 96 to 100 1-2 linked 4,6-dideoxy-4-formamido-α-D-mannopyranosyl units and having a molecular weight about 15,000 to 18,000.

2. The antigenic polysaccharide of claim 1 having about 100 of said mannopyranosyl units and a molecular weight of about 18,000.

3. The antigenic polysaccharide of claim 1 modified to have a hydrophobic moiety attached thereto.

4. The antigenic polysaccharide of claim 3 wherein said hydrophobic moiety is a fatty acid ester linked to the polysaccharide via the aliphatic chain.

5. The antigenic polysaccharide of claim 4 wherein said moiety is $-NH-(CH_2)_nCOOR$ where R is a lower alkyl group and n=7-17.

6. The antigenic polysaccharide of claim 5 wherein said moiety has the formula:

$-NH-(CH_2)_{11}COOCH_2CH_3$.

7. The antigenic polysaccharide of claim 1, adsorbed onto or coupled to a hydrophobic carrier.

8. The antigenic polysaccharide of claim 7 wherein the carrier is selected from hydrophobic polymers.

9. The antigenic polysaccharide-carrier combination of claim 8 wherein the carrier is an ELISA plate.

10. A method of preparing the antigenic polysaccharide of claim 1 suitable for detecting *Brucella abortus* or antibodies thereto, comprising:
    (a) growing *Yersinia enterocolitica* serotype 0:9 in a suitable growth medium, and recovering cells thereof,
    (b) isolating phenol-soluble lipopolysaccharide (LPS) from the cells,
    (c) cleaving the O-antigenic polysaccharide from the LPS with mild acid hydrolysis and removing the lipid portion, and
    (d) recovering the antigenic polysaccharide of claim 1.

11. A method of preparing the antigenic polysaccharide of claim 3 linked to a hydrophobic moiety suitable for detecting *Brucella abortus* or antibodies thereto, comprising:
    (a) growing *Yersinia enterocolitica* serotype 0:9 in a suitable growth medium, and recovering cells thereof,
    (b) isolating phenol-soluble lipopolysaccharide (LPS) from the cells,
    (c) cleaving the O-antigenic polysaccharide from the LPS with mild acid hydrolysis and removing the lipid portion,
    (d) modifying O-antigenic polysaccharide resulting from step (c) to yield a side group capable of covalent bonding with reactive groups of a hydrophobic moiety,
    (e) reacting the product of step (d) with a hydrophobic moiety to yield the modified antigen of claim 3.

12. The method of claim 11 wherein step (d) comprises subjecting the O-antigenic polysaccharide to periodate oxidation to yield aldehyde to periodate space oxidation to yield aldehyde groups capable of covalent bonding with amino groups of a hydrophobic variety.

* * * * *